(12) United States Patent
Van Acht et al.

(10) Patent No.: US 8,818,751 B2
(45) Date of Patent: Aug. 26, 2014

(54) INTERPRETING ANGULAR ORIENTATION DATA

(75) Inventors: Victor Martinus Gerardus Van Acht, Waalre (NL); Edwin Gerardus Johannus Maria Bongers, Thorn (NL); Nicolaas Lambert, Waalre (NL)

(73) Assignee: Koninklijke Philips N.V., Eindhoven (NL)

( * ) Notice: Subject to any disclaimer, the term of this patent is extended or adjusted under 35 U.S.C. 154(b) by 528 days.

(21) Appl. No.: 13/145,662

(22) PCT Filed: Jan. 14, 2010

(86) PCT No.: PCT/IB2010/050146
§ 371 (c)(1),
(2), (4) Date: Sep. 29, 2011

(87) PCT Pub. No.: WO2010/084440
PCT Pub. Date: Jul. 29, 2010

(65) Prior Publication Data
US 2012/0053890 A1    Mar. 1, 2012

(30) Foreign Application Priority Data
Jan. 22, 2009    (EP) .................................... 09151105

(51) Int. Cl.
G06F 15/00    (2006.01)
G01B 21/00    (2006.01)
A61B 5/103    (2006.01)
A61B 5/107    (2006.01)

(52) U.S. Cl.
CPC ............. *A61B 5/1038* (2013.01); *A61B 5/1071* (2013.01); *A61B 2562/0219* (2013.01)
USPC ............... 702/151; 702/150; 33/301; 33/343; 607/62; 600/595

(58) Field of Classification Search
CPC ............. A61B 2017/564; A61B 5/103; A61B 5/4528; A61B 5/06; A61B 5/1071; A61B 5/6828; A61F 2002/30538; A61F 2250/0006; A61F 2/30; A63B 2220/16
USPC ......... 702/150, 151; 33/301, 343; 607/17, 62; 600/301, 515, 595
See application file for complete search history.

(56) References Cited

U.S. PATENT DOCUMENTS 6,611,783 B2 *    8/2003    Kelly et al. .................... 702/150
7,383,728 B2 *    6/2008    Noble et al. ................ 73/379.01
(Continued)

FOREIGN PATENT DOCUMENTS

WO        0036520 A1    6/2000
WO     2007008930 A2    1/2007
(Continued)

OTHER PUBLICATIONS

Brunetti, F. et al "A New Platform based on IEEE802.15.4 Wireless Inertial Sensors for Motion Caption and Assessment" Engineering in Medicine and Biology Society, 2006, pp. 6497-6500.

*Primary Examiner* — Carol S Tsai

(57) ABSTRACT

The invention relates to method and a system of interpreting angular orientation data. It is determined, whether the angular deviation of a current angular orientation (C) of a sensor device (12) from a last extreme angular orientation (L) currently decreases after having increased before up to a provisional new extreme angular orientation (P), thereby determining that the provisional new extreme angular orientation (P) is a new extreme angular orientation. Information relating to a new extreme angular orientation, such as an angular range of motion, may be output to a user.

14 Claims, 4 Drawing Sheets

(56) References Cited

U.S. PATENT DOCUMENTS

| | | | |
|---|---|---|---|
| 8,351,894 B2* | 1/2013 | Fields et al. | 455/404.1 |
| 8,444,578 B2* | 5/2013 | Bourget et al. | 600/595 |
| 8,447,401 B2* | 5/2013 | Miesel et al. | 607/19 |
| 8,579,834 B2* | 11/2013 | Davis et al. | 600/595 |
| 2001/0032059 A1* | 10/2001 | Kelly et al. | 702/150 |
| 2002/0103610 A1* | 8/2002 | Bachmann et al. | 702/94 |
| 2004/0010390 A1* | 1/2004 | Kelly et al. | 702/150 |
| 2006/0251334 A1* | 11/2006 | Oba et al. | 382/275 |
| 2007/0015611 A1* | 1/2007 | Noble et al. | 473/450 |
| 2007/0038155 A1 | 2/2007 | Kelly | |
| 2008/0091373 A1 | 4/2008 | McGibbon | |
| 2008/0146969 A1* | 6/2008 | Kurtz | 600/595 |

FOREIGN PATENT DOCUMENTS

| | | |
|---|---|---|
| WO | 2008005330 A2 | 1/2008 |
| WO | 2008010131 A2 | 1/2008 |

* cited by examiner

INTERPRETING ANGULAR ORIENTATION DATA

FIELD OF THE INVENTION

The invention relates to a field of interpreting angular orientation data, and more specifically to interpreting angular orientation data of a body part and, more specifically, to determining an angular range of motion of a body part.

BACKGROUND OF THE INVENTION

From WO 2007/008930 A2, a method of monitoring a range of motion of a body part is known, wherein a housing including a sensor is positioned against said body part, and wherein, in a first measuring step, a first orientation of an apparent gravity force acting on said housing is obtained while said body part has a first orientation relative to adjoin to which said body part is coupled and, in a second measuring step, a second direction of the apparent gravity force acting on said housing is obtained, while said body part has a second orientation relative to the joint. In a determining step, a magnitude of rotation of said body part from the first orientation to the second orientation is determined based upon the first and second directions of said apparent gravity force.

SUMMARY OF THE INVENTION

In physiotherapy, an accurate and easy to use method or system for determining an angular range of motion is desirable, as the motivation of the patient is influenced tremendously by the progress that is being made. If the therapist can show the patient that he is improving his range of motion, even by only a few degrees, which is difficult to see by the naked eye, this motivates the patient.

However, setting up a mechanical goniometer for measuring the range of motion of a joint of a patient can be cumbersome. Furthermore, a goniometer may not be suitable to measure continuously during each repetition of a physiotherapy exercise.

For a movement of the body part in a vertical plane, the method of WO 2007/008930 A2 allows determining a magnitude of rotation of the body part independent of the alignment between the body part and the housing. However, in physical rehabilitation and evaluation applications, the method requires some interaction with the patient in order to manipulate the apparatus when the first and second positions are taken. This may involve calibration errors. Moreover, a movement about a vertical rotation axis cannot be recognized properly.

It would be desirable to determine extreme angular orientations and/or an angular range of motion of a body part during each repetition of a physical therapy exercise, and without interfering with or disturbing the physiotherapy exercise. It would also be desirable if no interaction of the patient and the system were required.

It would also be desirable to eliminate the need for a calibration procedure for calibrating the system. It would also be desirable to eliminate the need for aligning a sensor device with the body part, to which the sensor device is to be attached. Eliminating the need for calibration and/or alignment significantly reduces the set-up time of the system and thus makes the system easy to apply.

It would also be desirable to provide for determining an angular range of motion of a body part for any arbitrary orientation of the body part.

To better address one or more of these concerns, in a first aspect of the invention, a method of interpreting angular orientation data is provided, comprising the steps of:

receiving angular orientation data from a sensor device, said angular orientation data comprising information about a current angular orientation in space of the sensor device relative to a reference orientation; and determining whether the angular deviation of the current angular orientation from a last extreme angular orientation currently decreases after having increased before up to a provisional new extreme angular orientation, thereby determining that the provisional new extreme angular orientation is a new extreme angular orientation.

For example, the above steps are repeated until a new extreme angular orientation has been determined. Thus, a reversal of an angular motion of the body part is detected and the angular orientation at the reversal is identified is a new extreme angular orientation. Therefore, the physiotherapy exercise of a patient is not disturbed and no interaction with the patient is required.

For example, an angular range of motion is determined as an angular difference between the new extreme angular orientation and the last extreme angular orientation.

For example, the sensor device is attached to a body part. For example, the body part is connected to a joint and is rotatable around a rotation axis of the joint with a certain range of motion. For example, a current angular orientation of a body part rotating around a joint axis of a joint connecting the body part is determined.

For example, the above steps are repeated, wherein, if a new extreme angular orientation has been determined, the new extreme angular orientation replaces the last extreme angular orientation. Thus, when the patient performs a repetitive movement, a series of extreme angular orientations may be determined.

When repeating the abovementioned steps, the reference orientation remains the same. However, the reference orientation may be unknown. For example, the reference orientation may be an initial orientation of the sensor device. Alternatively, the reference orientation may be a vertical upright orientation, i.e. opposite to the orientation of gravity.

Said angular deviation is, for example, the angle between said orientations. For example, the angular deviation is a true angular deviation, e.g. independent of the actual orientation(s). For example, the angular deviation is calculated in degrees or radians.

Further useful details of the invention are indicated in the dependent claims.

In one embodiment, the sensor device is, in any angular orientation, sensitive for rotation about each of a vertical axis and two further axes. Thus, no direction of the movement relative to the sensor device is prescribed. For example, said information about a current angular orientation in space of the sensor device includes yaw (heading), pitch and roll angles.

In one embodiment, the angular deviation is a deviation in three-dimensional rotational space. In particular, the angular deviation may comprise a rotation around the vertical axis ("heading" information). Thus, no direction of movement of the body part is prescribed. For example, the method allows determining extreme angular orientations of a lower leg while the patient is lying on his side and moves his lower leg about his knee. Thus, an angular range of motion around an arbitrary rotation axis may be determined. Typically, an angular range of motion around a joint axis of a joint connecting the body part is determined.

Differences between angular orientations may be determined independent of the reference orientation. No knowledge about an absolute orientation of the sensor device in relation to a stationary axis is required. For example, in the determining step, only angular differences between respective angular orientations are compared in determining whether the angular deviation of the current angular orientation from a last extreme annular orientation currently decreases after having increased before.

Furthermore, in the method, and, in particular in the determining step, no knowledge about a relative orientation of the sensor device and the body part is required. However, the relative orientation of the sensor device in the body part is fixed.

The method is independent of the orientation or alignment of the sensor device relative to the direction of the angular motion of the body part. Thus, the sensor device may be attached to the body part at an arbitrary position and orientation.

Typically, the new extreme angular orientation is at an opposite end of an angular orientation range extending between the last extreme angular orientation and the new extreme angular orientation. It should be noted however, that, in determining a new extreme angular orientation, only those angular orientations, which are actually measured by and received from the sensor device are taken into account. With a sufficiently high repeat rate or sample rate of the sensor device, however, the actual extreme angular orientations can be determined with high accuracy.

In one embodiment, the method further comprises the step of outputting information relating to the new extreme angular orientation to a user. For example, said output information may be information relating to an angular range of motion or an angular difference between the new extreme angular orientation and the last extreme angular orientation. For example, the information may be displayed on a display. For example, the output information may include a sign indicating the direction of the movement, such as "+" for forward and "−" for backward. Additionally or alternatively, said information relating to the new extreme angular orientation comprises an angular difference between the new extreme angular orientation and a last but one extreme angular orientation and/or at least one further, previous extreme angular orientation.

In one embodiment, in the determining step, a current angular orientation, which corresponds to a currently decreasing deviation of the current angular orientation from the last extreme angular orientation, is only taken into account if the angular difference between the current angular orientation and the provisional new extreme angular orientation exceeds a threshold value. By appropriately selecting the threshold value, it can be made sure that small tremors in the movement do not trigger a new extreme. Thus, the global extreme angular orientations are found, while small local extremes are not registered. The threshold value is a tuning parameter. If it is chosen larger, larger tremors can be allowed before a new extreme is triggered, but intended movements smaller than the threshold value are not detected by the method.

In one embodiment, the determining step comprises the steps of or consists of the steps of:
  determining whether an angular deviation between the current orientation and the last extreme orientation is larger than an angular deviation between the provisional new extreme orientation and the last extreme orientation, and, if so, setting the provisional new extreme orientation to the value of the current orientation;
  determining whether an angular deviation between the current orientation and the provisional new extreme orientation exceeds a threshold value, and, if so, setting the last extreme orientation to the value of the provisional new extreme orientation and setting the provisional new extreme orientation to the value of the current orientation.

In a second aspect of the invention, a system for interpreting angular orientation data of a body part is provided, the system comprising:
  a sensor device for being attached to the body part; and
  an interpreter device, the interpreter device being arranged for:
  receiving angular orientation data from the sensor device, said angular orientation data comprising information about a current angular orientation in a space of the sensor device relative to a reference orientation; and
  determining whether the angular deviation of the current angular orientation from a last extreme angular orientation currently decreases after having increased before up to a provisional new extreme angular orientation, thereby determining that the provisional new extreme angular orientation is a new extreme angular orientation.

In one embodiment, the system further comprises an output device for outputting to a user information relating to a new extreme angular orientation.

For example, the sensor device is, in any angular orientation, sensitive for rotation about each of a vertical axis and two further axes.

For example, the interpreter device is arranged for performing the method described above. For example, the interpreter device may comprise a computer for executing a computer program for performing the method as described above.

DETAILED DESCRIPTION OF EMBODIMENTS

Figure 1:
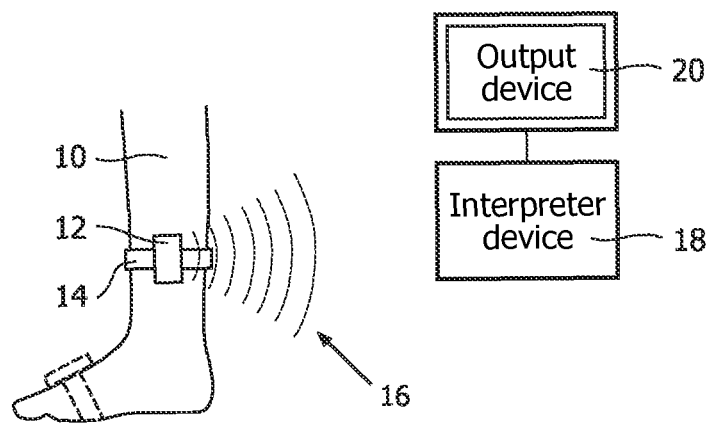
FIG. 1 schematically illustrates a system for interpreting angular orientation data according to the invention, the system having a sensor device, which is attached to a body part.

FIG. 1 exemplarily shows a system for interpreting angular orientation data of a body part 10. For example, the body part is a lower leg of a patient. A sensor device 12 is attached to the body part 10, for example using a textile elastic strap 14. Thus, the patient can easily attach the sensor device 12 to his own lower leg or other body part, the motion of which is to be monitored.

The sensor device 12 comprises, for example, various sensors for measuring angular orientation of the sensor device in three dimensions. For example, the sensor device 12 may include a 3D-accelerometer for measuring gravity and a 3D-magnetometer for measuring the earth magnetic field to provide a static drift free orientation. Furthermore, the sensor device 12 may comprise three gyroscopes to track fast changes in orientation. Such a sensor device is, for example, the Philips PI-node or the Xsens MTx orientation tracker.

Because the sensor includes a 3D-accelerometer, the sensor device can measure tilt (rotation around two horizontal axes) independently of the sensor orientation. Because the sensor device includes a 3D-magnetometer, it can measure heading (rotation around the vertical axis) independently of the orientation of the sensor device. The sensor includes, for example, an algorithm for combining the different measurement signals into 3D orientation estimation data.

For example, the sensor device 12 is arranged to output angular orientation data comprising information about the current angular orientation in space of the sensor device relative to a vertical upright reference orientation. However, the reference orientation is not necessarily calibrated.

For example, the sensor device 12 outputs a signal 16, for example a radio signal, for transmitting the current angular orientation data.

An interpreter device 18, which for example includes a computer, receives the signal 16 and interprets the angular orientation data as will be described below with reference to FIGS. 3 to 6.

The interpreter device 18 is arranged for outputting to a user information gained by the interpreter device 18 via an output device 20. The output device 20 is, for example, a display.

Figure 2:
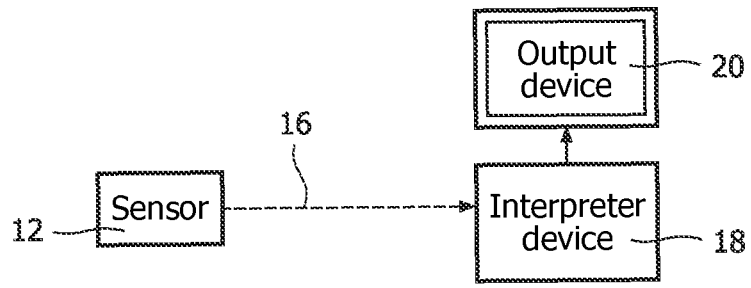
FIG. 2 schematically illustrates a system for interpreting angular orientation data according to the invention.

FIG. 2 schematically illustrates a signal flow from the sensor device 12 to a interpreter device 18, and the output information flow from the interpreter device 18 to the output device 20. Instead of a radio signal, the signal 16 may also transmitted via one or more electric lines of a cable connection. Furthermore, the interpreter device 18 may be included in the sensor device 12. For example, information gained by the interpreter device 18 may be output via a radio signal. Furthermore, for example, the output device 20 may be included in the sensor device 12. Additionally or alternatively to a display, the output device 20 may include a speaker for outputting a voice message, e.g. a synthesized voice, for outputting said information. For example, the system may consist of an integrated device and, optionally, attachment means such as the textile elastic strap 14.

The interpreter device 18 is arranged for performing a method of interpreting the angular orientation data received from the sensor device 12, which method will be explained in the following with reference to FIGS. 3 to 6.

Figure 3:
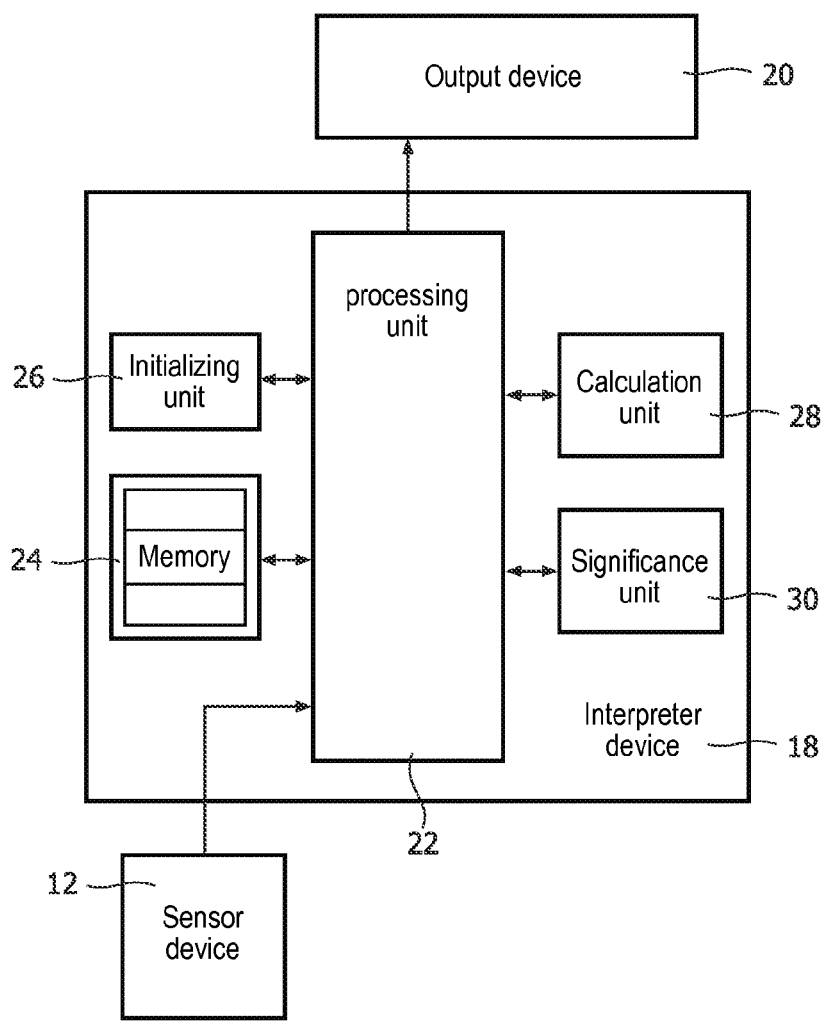
FIG. 3 is a detailed schematical illustration of a system for interpreting angular orientation data according to the invention.
Figure 4:
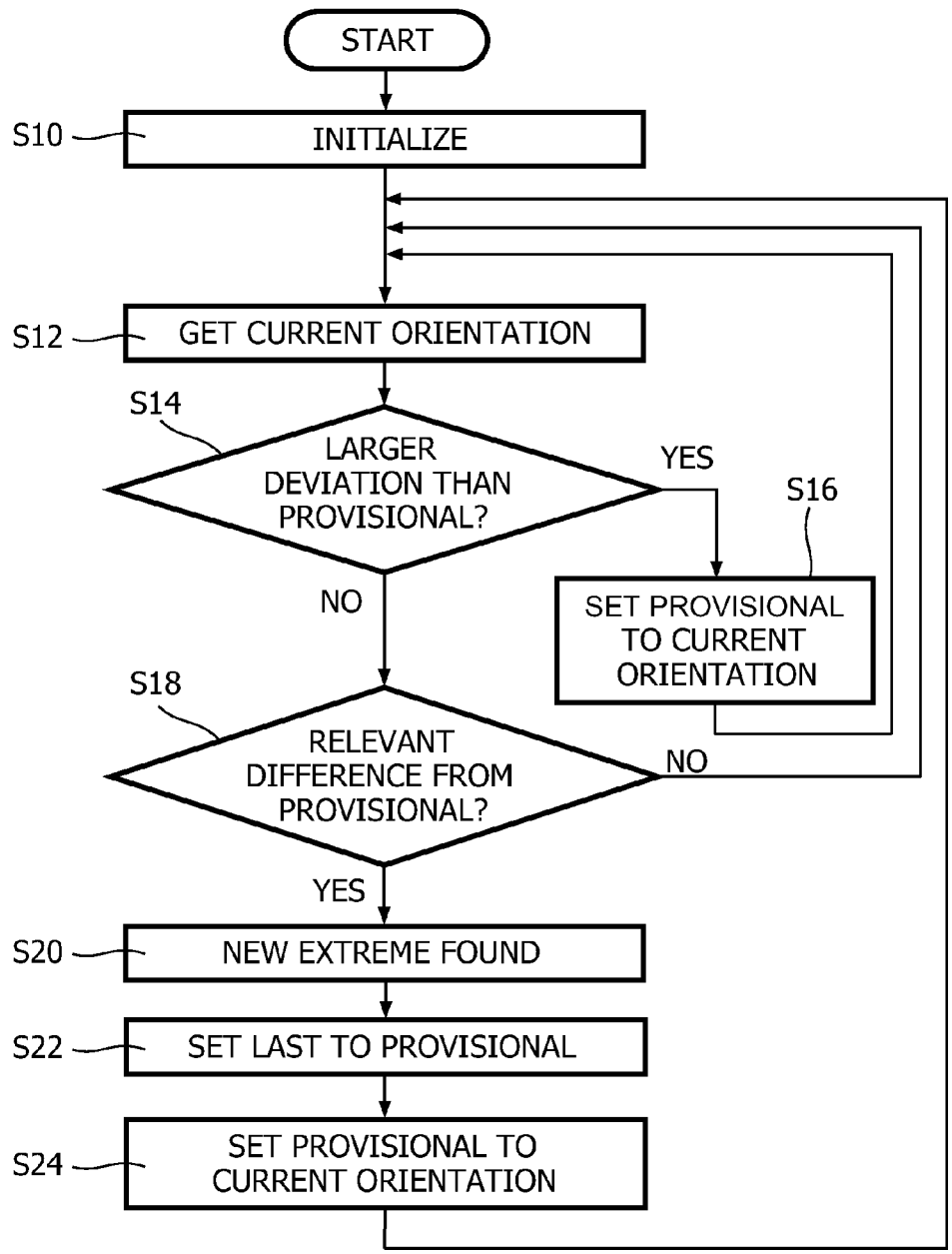
FIG. 4 is a diagram illustrating a method of interpreting angular orientation data according to the invention.

FIG. 3 schematically illustrates the system according to the invention including the sensor device 12, the interpreter device 18 and the output device 20. A processing unit 22 of the interpreter device 18 executes a computer program for performing said method as is schematically illustrated in the diagram of FIG. 4.

In an initializing step S10, the processing unit 22 initializes orientations which are stored as variables in a memory 24. These orientations include LAST_EXTREME_ORIENTATION, PROVISIONAL_NEW_EXTREME_ORIENTATION and CURRENT_ORRIENTATION. In the following, these are also expressed as LAST, PROVISIONAL and CURRENT, or as the last extreme orientation, the provisional new extreme orientation and the current orientation.

For example, the orientations are stored as quaternions [w, x, y, z].

For example, in step S10 LAST is initialized to the unit quaternion [1, 0, 0, 0], and PROVSIONAL is also initialized to [1, 0, 0, 0]. The initializing step S10 is, for example, controlled by an initializing unit 26 of the computer program.

In step S12, the processing unit 22 receives angular orientation data from the sensor device 12, said data comprising information about a current angular orientation in space of the sensor device, which orientation is stored, for example, as a quaternion, as the orientation CURRENT.

In step S14, a difference calculation unit 28 of the computer program is used to calculate the angular difference between the current orientation and the last extreme orientation and to calculate an angular difference between the provisional new extreme orientation and the last extreme orientation.

For example, the difference 6 between two orientations, expressed as quaternions $[w_1, x_1, y_1, z_1]$ and $[w_2, x_2, y_2, z_2]$, may be defined as $\delta 6 = 2 \arccos(|w_1 w_2 + x_1 x_2 + y_1 y_2 + z_1 z_2|)$. Thus, $\delta$ is the true angular difference between the two orientations, expressed in degree or radians. The calculated differences are then compared. If the angular deviation of the current angular orientation from the last extreme angular orientation is larger than the angular deviation of the provisional extreme angular orientation from the last extreme angular orientation, step S16 is executed. This case is illustrated in FIG. 5.

Figure 5:
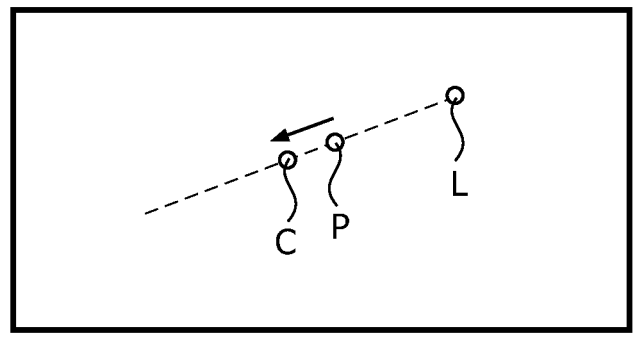
FIGS. 5 and 6 are diagrams illustrating steps of the method.
Figure 6:
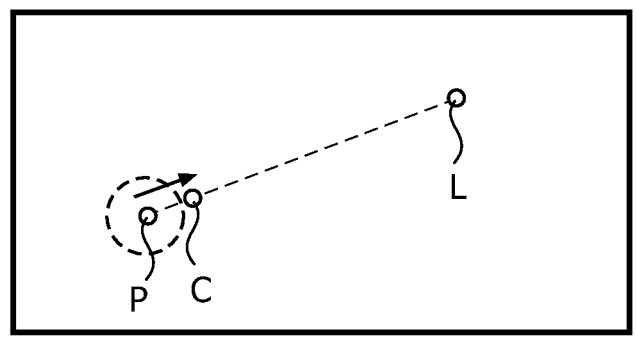

In FIGS. 5 and 6, orientations are schematically illustrated in an orientational space. Only two angular dimensions are shown for illustrating purposes. A repetitive angular motion of the sensor device is indicated by a dashed line. The last extreme orientation is indicated as L, the provisional new extreme orientation is indicated as P, and the current angular orientation is indicated as C. The direction of angular motion is indicated by an arrow.

In step S16, the provisional new extreme angular orientation is set to the current angular orientation. After step S16, the program is repeated from step S12 on.

If in step S14 the angular deviation of the current angular orientation from the last extreme angular orientation is not larger than the angular deviation of the provisional new angular orientation from the last extreme angular orientation, step S18 is executed.

In step S18, a significance unit 30 of the computer program checks whether the angular difference between the current angular orientation and the provisional new angular orientation, calculated by the difference calculation unit 28, is larger than a threshold value. For example, the threshold value is smaller than 10 degrees. For example, the threshold value may be 5 degrees, or even smaller.

If the threshold value is exceeded, a new extreme angular orientation has been found, and step S20 is executed. This situation is illustrated in FIG. 6.

In FIG. 6, a circle drawn around the provisional new extreme orientation P is shown, the radius of which indicates the threshold value. In this situation, the provisional new extreme orientation marks a reversal of the angular motion.

In step S20, for example, a message indicating the angular range of motion between the last extreme angular orientation and the provisional new extreme angular orientation is output on the output device 20. For example, the message may be "65 degrees range of motion", "−65 degrees" or "+3 degrees further than last time". In the latter case, a difference between the provisional new extreme orientation and the last but one extreme orientation has been calculated in order to compare extreme angular orientations achieved in the same angular direction of motion.

If in step S18 the calculated deviation does not exceed the threshold value, i.e. the orientation C lies within the circle around the orientation P in FIG. 6, the current orientation is not taken into account, and the steps of the program are repeated beginning with step S12.

In step S22, LAST is set to PROVISIONAL, and in step S24, PROVISIONAL is set to CURRENT. Thus, the provisional new extreme orientation replaces the last extreme orientation, and the value of the provisional new extreme orientation is again initialized. Then, the program is repeated beginning with step S12.

Thus, in steps S14 and S18, it is determined whether the angular deviation of the current angular orientation from the last extreme angular orientation current decreases after having increased before up to the provisional new extreme angular orientation. Due to the relevance test in step S18, it is made sure that small tremors in the movement do not trigger the determination of a new extreme orientation.

While the invention has been illustrated and described in detail in the drawings and foregoing description, such illustration and description are to be considered illustrative or exemplary and not restrictive. The invention is not limited to the disclosed embodiments.

Variations to the disclosed embodiments can be understood and effected by those skilled in the art in practicing the claimed invention, from a study of the drawings, the disclosure, and the appended claims. For example, instead of representing the orientations as quaternions, Euler angles or rotation matrixes may be employed as well, using an adequately defined angular difference calculation function. Moreover, the steps of FIG. 4 may be executed in a different order, and other variables may be used. For example, angular deviations may be stored in memory.

Furthermore, all the disclosed elements and features of each disclosed embodiment of the method or the system can be combined with, or substituted for, the disclosed elements and features of every other disclosed embodiment of the method or the system, except where such elements or features are mutually exclusive. The mere fact that certain measures are recited in mutually different dependent claims does not indicate that a combination of these measures cannot be used to advantage.

In the claims, the word "comprising" does not exclude other elements or steps, and the indefinite article "a" or "an" does not exclude a plurality. Any reference signs in the claims should not be construed as limiting the scope.

The invention claimed is:

1. A method of interpreting angular orientation data, comprising the steps of:
   receiving angular orientation data from a sensor device, said angular orientation data comprising information about a current angular orientation in space of the sensor device relative to a reference orientation; and
   determining whether the angular deviation of the current angular orientation from a last extreme angular orientation currently decreases after having increased before up to a provisional new extreme angular orientation, thereby determining that the provisional new extreme angular orientation is a new extreme angular orientation.

2. The method as claimed in claim 1, wherein said sensor device is, in any angular orientation, sensitive for rotation about each of a vertical axis and two further axes.

3. The method as claimed in claim 1, wherein the angular deviation is a deviation in three-dimensional rotational space.

4. The method as claimed in claim 1, further comprising the step of:
   determining an angular range of motion as an angular difference between the new extreme angular orientation and the last extreme angular orientation.

5. The method as claimed in claim 1, the method further comprising the step of:
   outputting information relating to the new extreme angular orientation to a user.

6. The method as claimed in claim 1, wherein in the determining step, a current angular orientation, which corresponds to a currently decreasing deviation of the current angular orientation from the last extreme angular orientation, is only taken into account if the angular difference between the current angular orientation and the provisional new extreme angular orientation exceeds a threshold value.

7. The method as claimed in claim 1, wherein the determining step comprises the steps of:
   determining whether an angular deviation between the current orientation and the last extreme orientation is larger than an angular deviation between the provisional new extreme orientation and the last extreme orientation, and, if so, setting the provisional new extreme orientation to the value of the current orientation;
   determining whether an angular deviation between the current orientation and the provisional new extreme orientation exceeds a threshold value, and, if so, setting the last extreme orientation to the value of the provisional new extreme orientation and setting the provisional new extreme orientation to the value of the current orientation.

8. A system for interpreting angular orientation data of a body part, the system comprising:
   a sensor device for being attached to the body part; and
   an interpreter device, the interpreter device being arranged for:
   receiving angular orientation data from the sensor device, said angular orientation data comprising information about a current angular orientation in space of the sensor device relative to a reference orientation; and
   determining whether the angular deviation of the current angular orientation from a last extreme angular orientation currently decreases after having increased before up to a provisional new extreme angular orientation, thereby determining that the provisional new extreme angular orientation is a new extreme angular orientation.

9. The system as claimed in claim 8, the system further comprising:
   an output device for outputting to a user information relating to a new extreme angular orientation.

10. The system as claimed in claim 8, wherein the interpreter device is adapted for receiving angular orientation data from the sensor device, said angular orientation data comprising information about a current angular orientation in space of the sensor device relative to a reference orientation; and
   determining whether the angular deviation of the current angular orientation from a last extreme angular orientation currently decreases after having increased before up to a provisional new extreme angular orientation, thereby determining that the provisional new extreme angular orientation is a new extreme angular orientation.

11. The system as claimed in claim 8, wherein said sensor device is, in any angular orientation, sensitive for rotation about each of a vertical axis and two further axes.

12. Computer program or Computer program product for performing the method as claimed in claim 1 when executed on a computer.

13. Data Carrier including a Computer program for performing the steps of the method as claimed in claim 1.

14. Computer for executing a computer program as claimed in claim 12.

* * * * *